US011457922B2

United States Patent
Montidoro et al.

(10) Patent No.: US 11,457,922 B2
(45) Date of Patent: Oct. 4, 2022

(54) MEDICAL DEVICE DELIVERY MEMBER WITH FLEXIBLE STRETCH RESISTANT DISTAL PORTION

(71) Applicant: DePuy Synthes Products, Inc., Raynham, MA (US)

(72) Inventors: Tyson Montidoro, Raynham, MA (US); Zhixian Chen, Raynham, MA (US); Daniel Solaun, Raynham, MA (US); David Blumenstyk, Raynham, MA (US); Juan Lorenzo, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 205 days.

(21) Appl. No.: 16/749,578

(22) Filed: Jan. 22, 2020

(65) Prior Publication Data
US 2021/0219981 A1 Jul. 22, 2021

(51) Int. Cl.
*A61B 17/12* (2006.01)
*A61B 17/00* (2006.01)

(52) U.S. Cl.
CPC .. *A61B 17/12113* (2013.01); *A61B 17/12009* (2013.01); *A61B 17/1214* (2013.01); *A61B 17/12163* (2013.01); *A61B 2017/00309* (2013.01); *A61B 2017/00871* (2013.01); *A61B 2017/12054* (2013.01)

(58) Field of Classification Search
CPC ........ A61B 17/12113; A61B 17/12009; A61B 17/1214; A61B 17/12163; A61B 2017/00309; A61B 2017/00871; A61B 2017/12054; A61B 2017/1205; A61B 2090/3966; A61B 17/12145; A61B 17/12031; A61M 25/0138; A61M 25/0105
See application file for complete search history.

(56) References Cited

U.S. PATENT DOCUMENTS

| 3,429,408 A | 2/1969 | Maker et al. |
| 5,108,407 A | 4/1992 | Geremia et al. |
| 5,122,136 A | 6/1992 | Guglielmi et al. |
| 5,250,071 A | 10/1993 | Palermo |
| 5,263,964 A | 11/1993 | Purdy |

(Continued)

FOREIGN PATENT DOCUMENTS

| EP | 1985244 A2 | 10/2008 |
| EP | 2498691 | 9/2012 |

(Continued)

*Primary Examiner* — Kathleen S Holwerda
*Assistant Examiner* — Lauren Dubose
(74) *Attorney, Agent, or Firm* — Troutman Pepper Hamilton Sanders LLP

(57) ABSTRACT

A delivery member is provided for delivering and deploying an intravascular medical device. The delivery member includes a flexible distal portion including a wound wire coil surrounded by a flexible sleeve and inhibited from extending lengthwise by a stretch resistant member positioned through the lumen of the coil. The delivery member can include hypotubes positioned on either side (distally and proximally) from the wound wire coil to which the stretch resistant member and the wound wire coil can be attached. The distal hypotube can include attachment slots for positioning and attaching a loop wire to the distal hypotube.

12 Claims, 6 Drawing Sheets

(56) References Cited

U.S. PATENT DOCUMENTS

| | | |
|---|---|---|
| 5,334,210 A | 8/1994 | Gianturco |
| 5,350,397 A | 9/1994 | Palermo et al. |
| 5,382,259 A | 1/1995 | Phelps et al. |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2003/0009208 A1 | 1/2003 | Snyder et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1* | 5/2006 | Fahey .............. A61M 25/0051 623/1.11 |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0312748 A1 | 12/2009 | Johnson et al. |
| 2010/0114017 A1 | 5/2010 | Lenker et al. |
| 2010/0324649 A1 | 12/2010 | Mattsson |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0283768 A1 | 11/2012 | Cox et al. |
| 2013/0066413 A1 | 3/2013 | Jin et al. |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0277084 A1 | 9/2014 | Mirigian et al. |
| 2014/0277085 A1* | 9/2014 | Mirigian .......... A61B 17/12113 606/200 |
| 2014/0277092 A1 | 9/2014 | Teoh et al. |
| 2014/0277093 A1 | 9/2014 | Guo et al. |
| 2015/0005808 A1 | 1/2015 | Chouinard et al. |
| 2015/0025562 A1 | 1/2015 | Dinh et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0157869 A1 | 6/2016 | Elgård et al. |
| 2016/0228125 A1 | 8/2016 | Pederson, Jr. et al. |
| 2016/0310304 A1 | 10/2016 | Mialhe |
| 2016/0346508 A1 | 12/2016 | Williams et al. |

(56) References Cited

U.S. PATENT DOCUMENTS

| | | |
|---|---|---|
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0325706 A1 | 11/2018 | Hebert et al. |
| 2019/0159784 A1 | 5/2019 | Sananes et al. |
| 2019/0192162 A1 | 6/2019 | Lorenzo |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0187951 A1 | 6/2020 | Blumenstyk |
| 2021/0001082 A1 | 1/2021 | Lorenzo et al. |

FOREIGN PATENT DOCUMENTS

| | | |
|---|---|---|
| EP | 3092956 A1 | 11/2016 |
| EP | 3501427 A1 | 6/2019 |
| JP | 2006-334408 A | 12/2006 |
| JP | 2012-523943 A | 10/2012 |
| JP | 2013-78584 A | 5/2013 |
| WO | 2009/132045 A2 | 10/2009 |
| WO | WO 2012/158152 A1 | 11/2012 |
| WO | 2017/066386 A1 | 4/2017 |
| WO | WO 2018/022186 A1 | 2/2018 |

* cited by examiner

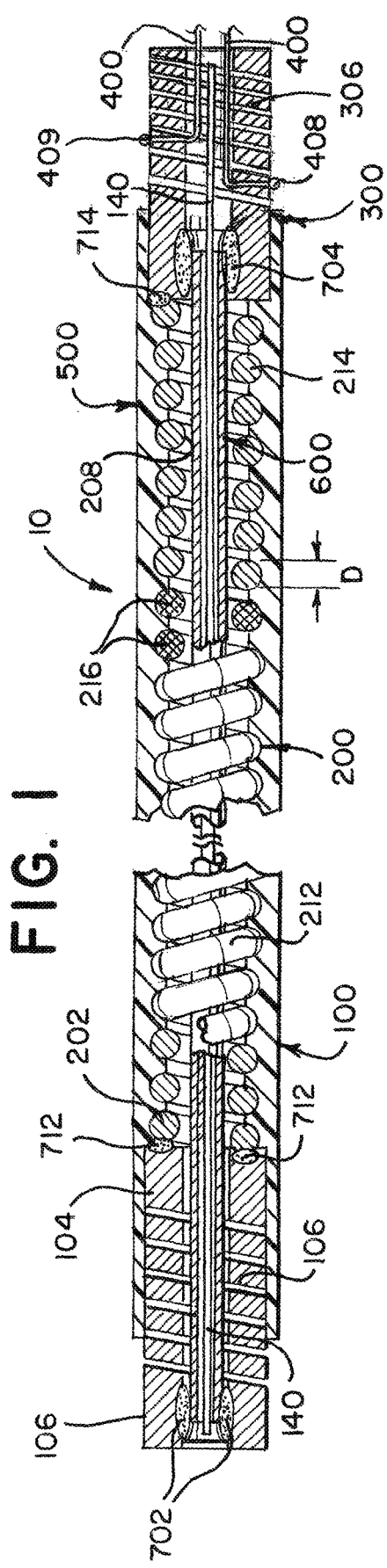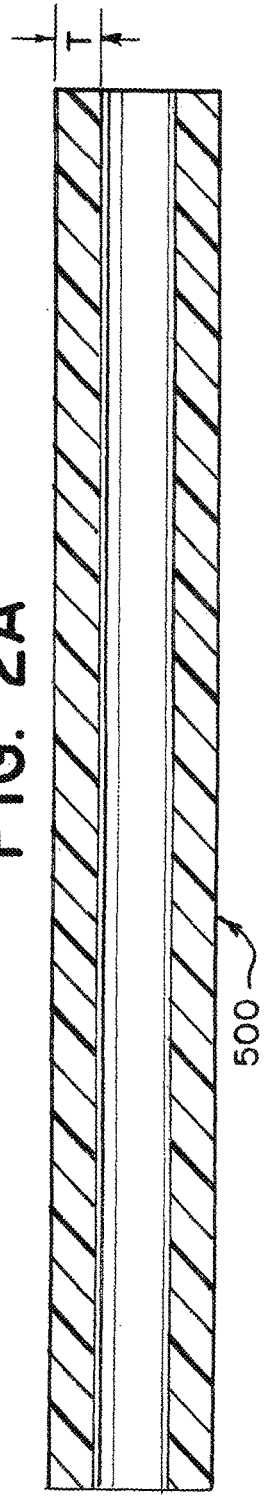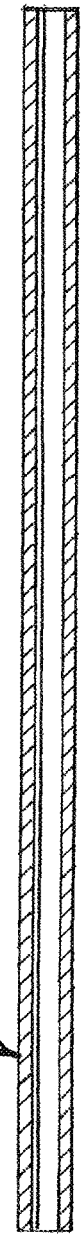

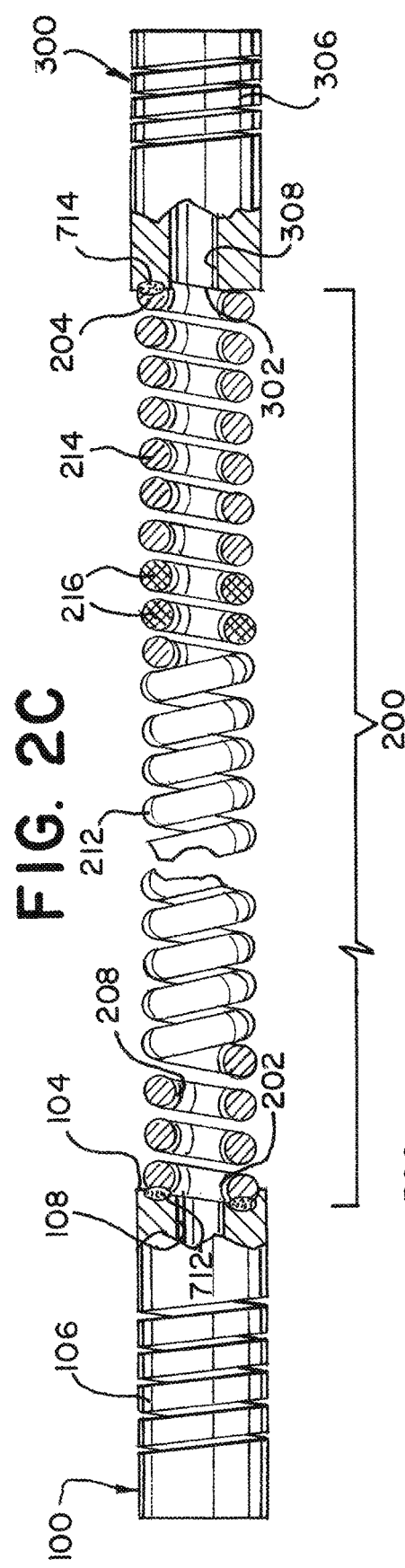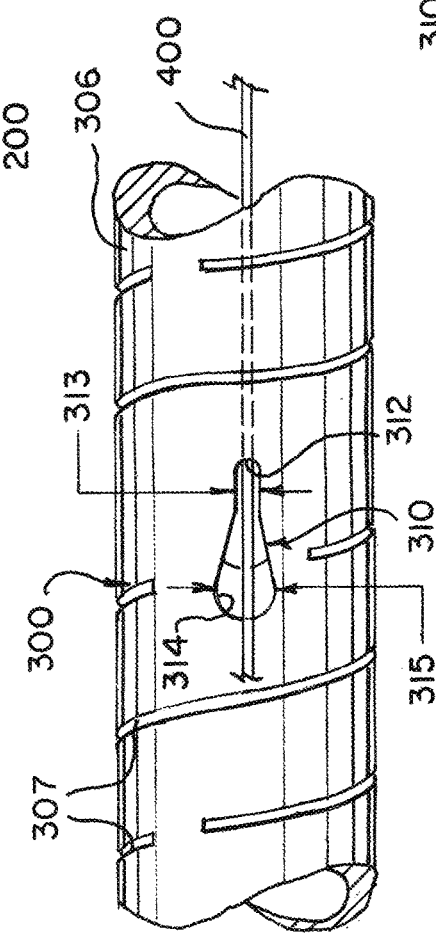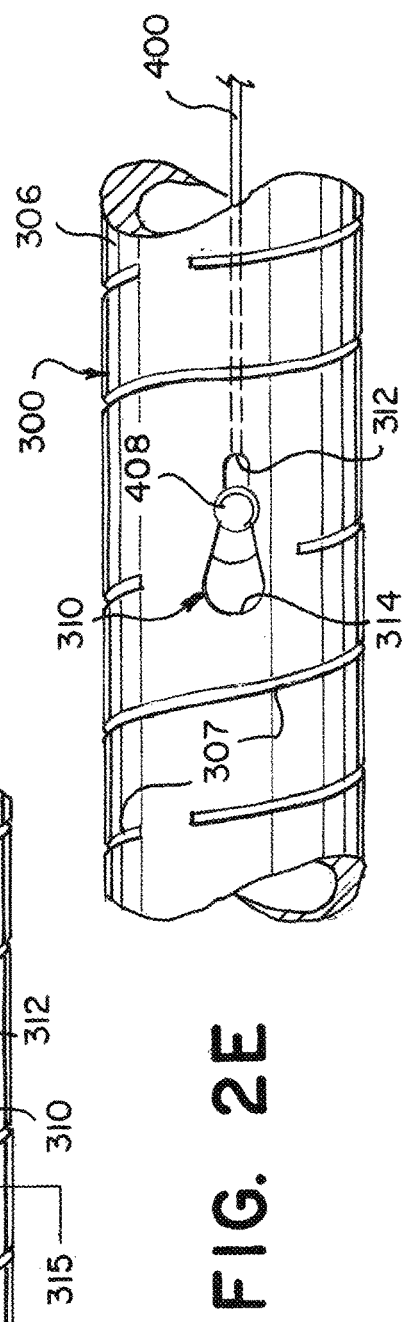

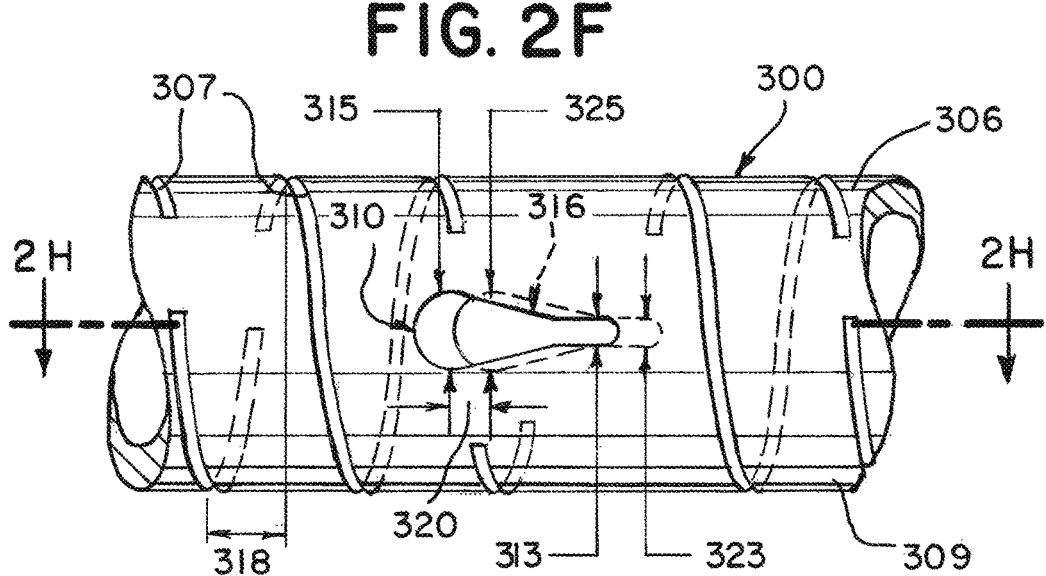
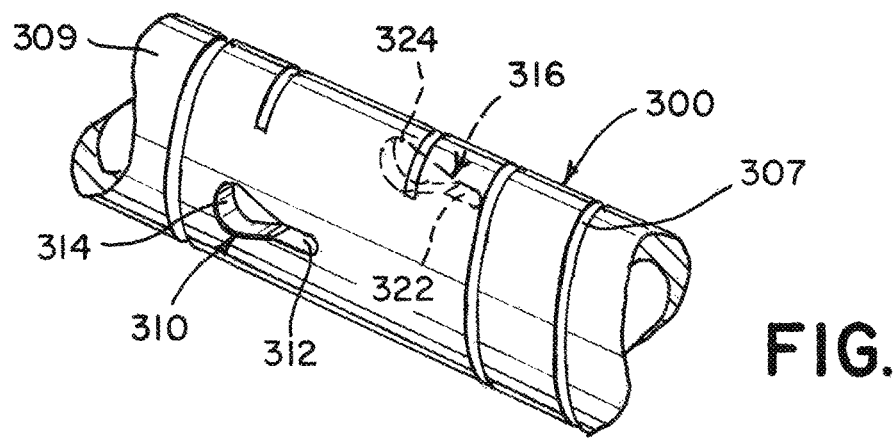
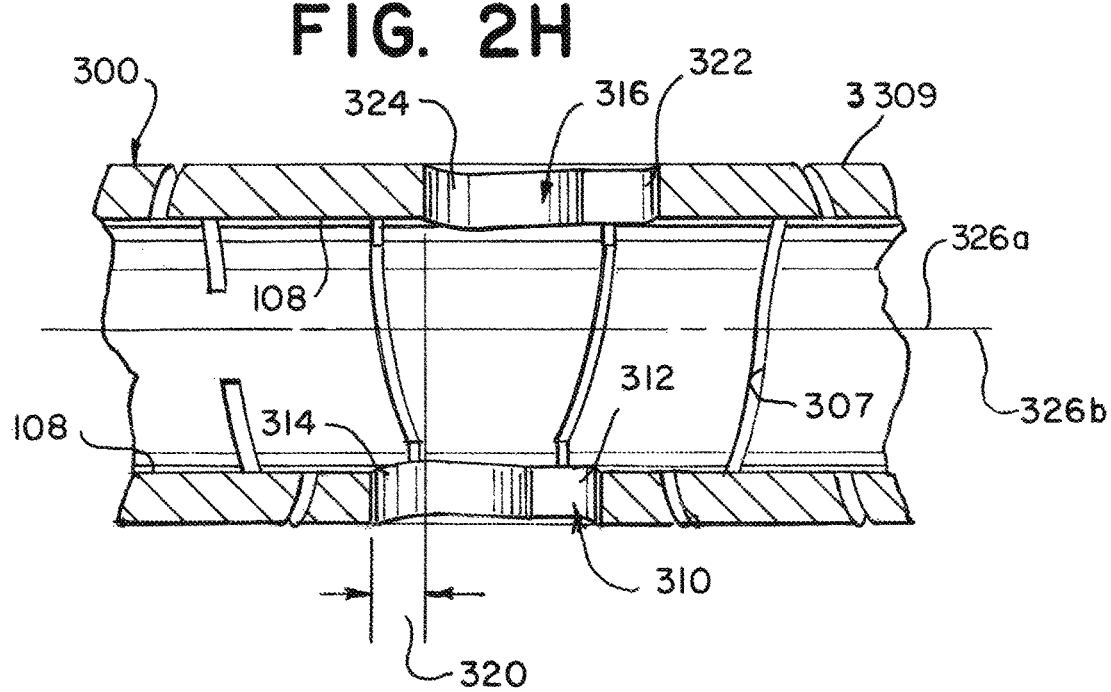

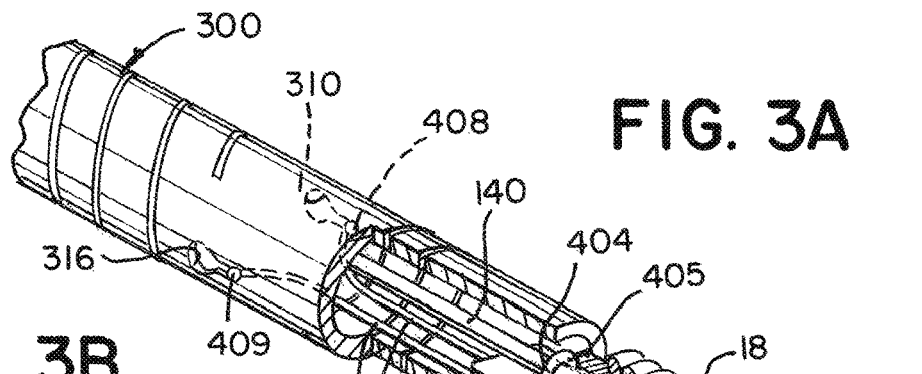
FIG. 3A
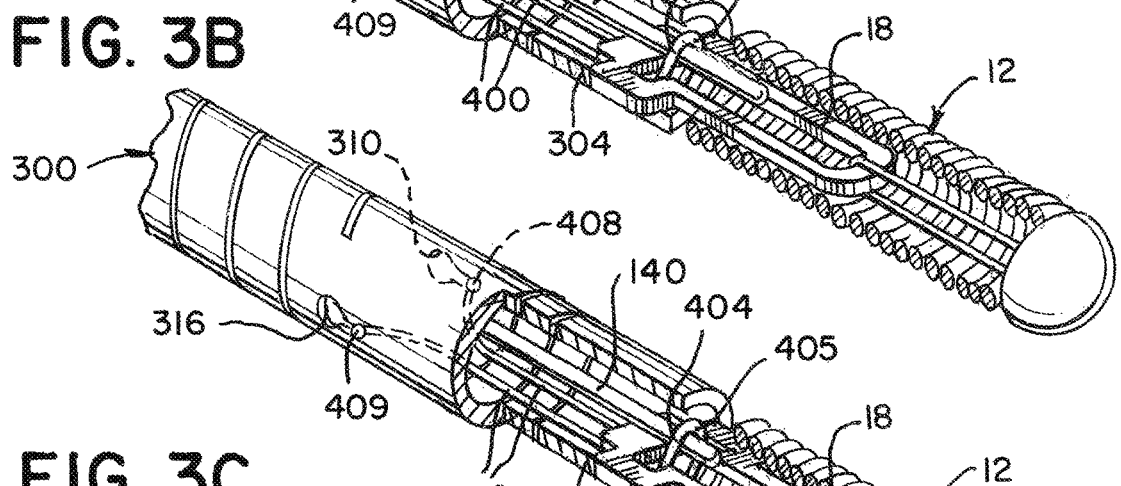
FIG. 3B
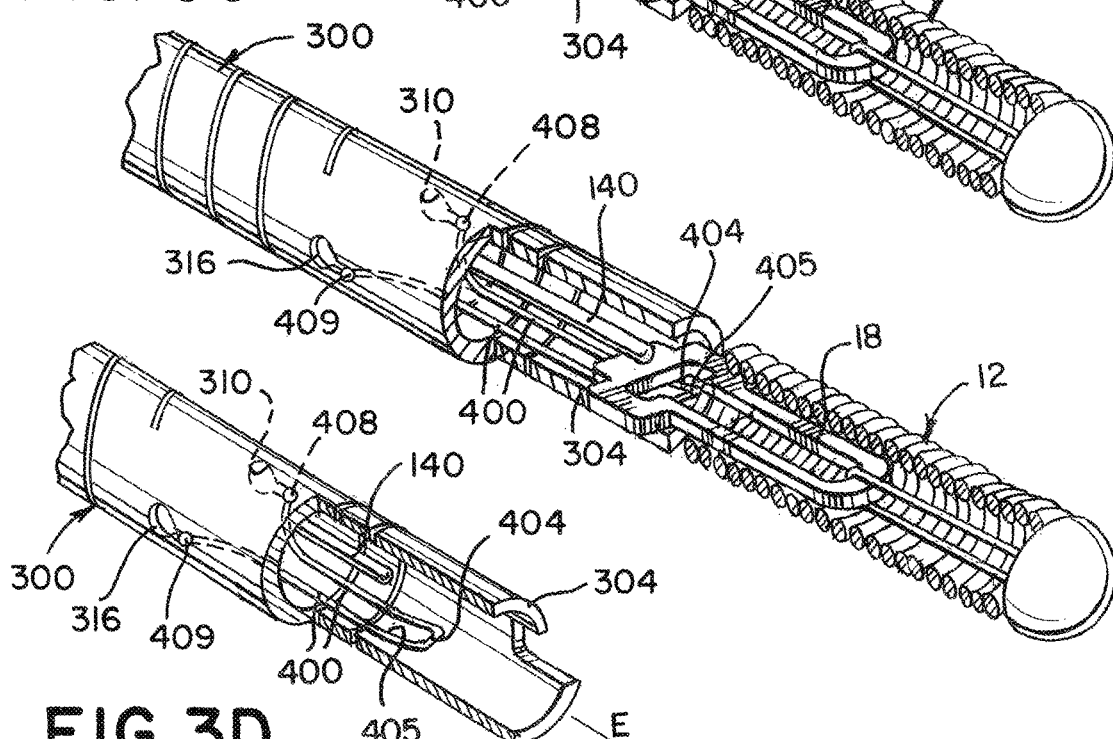
FIG. 3C
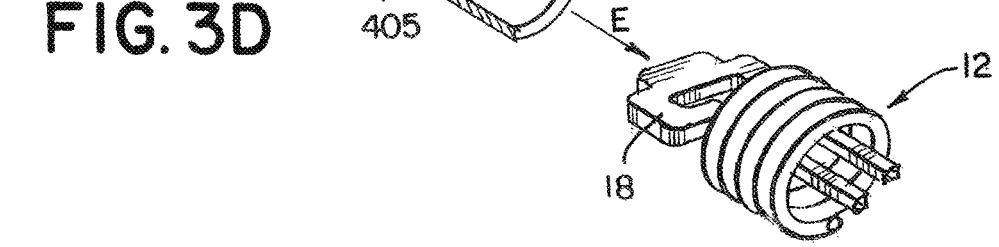
FIG. 3D
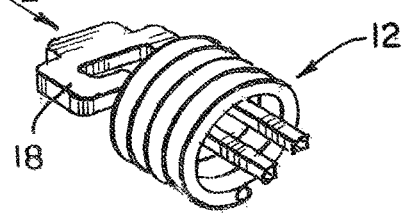

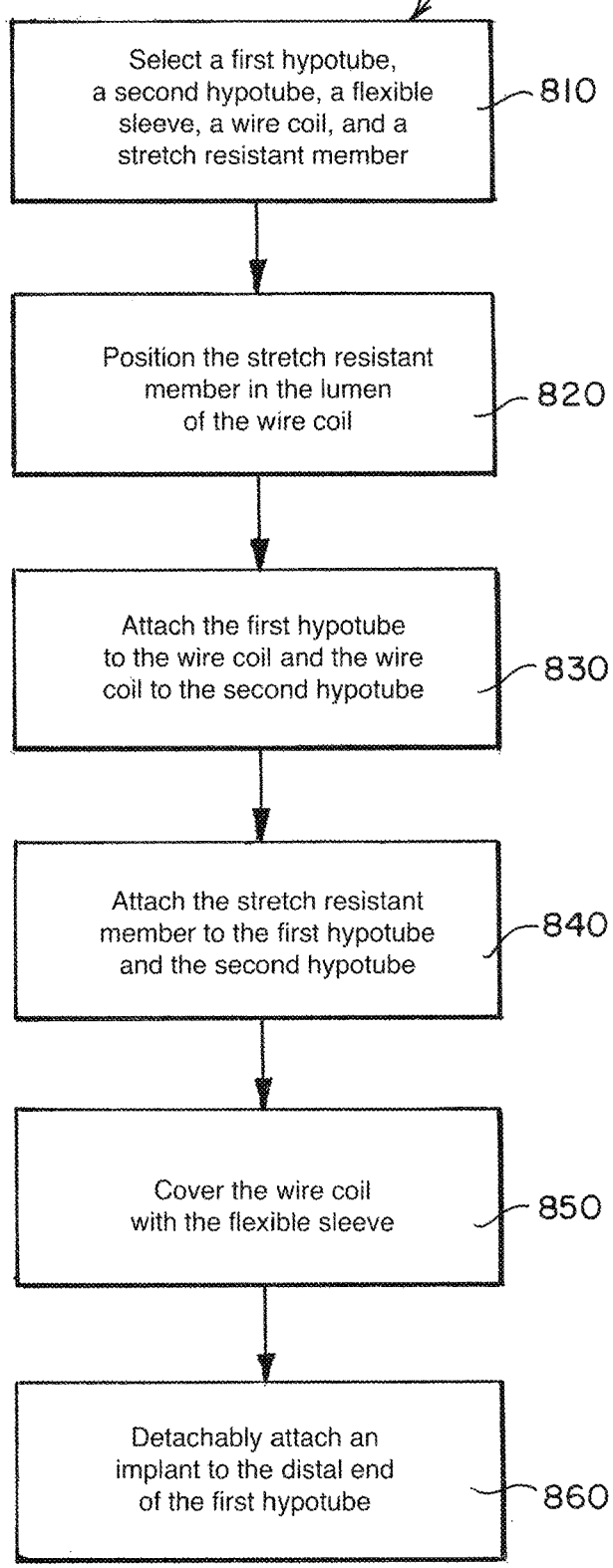
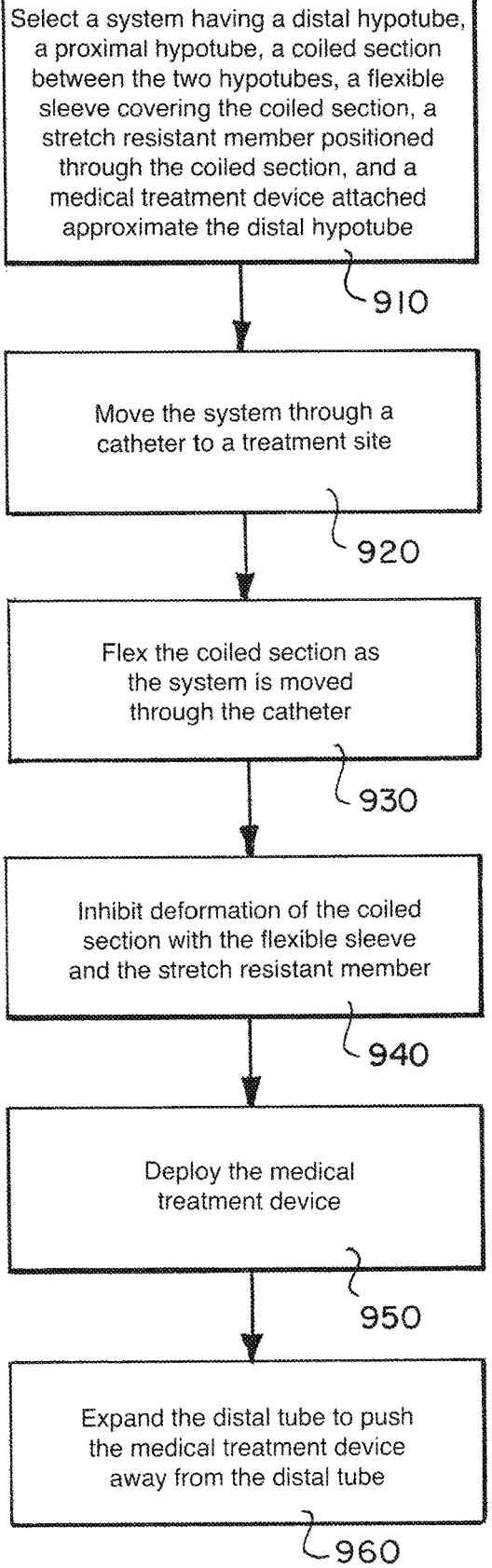

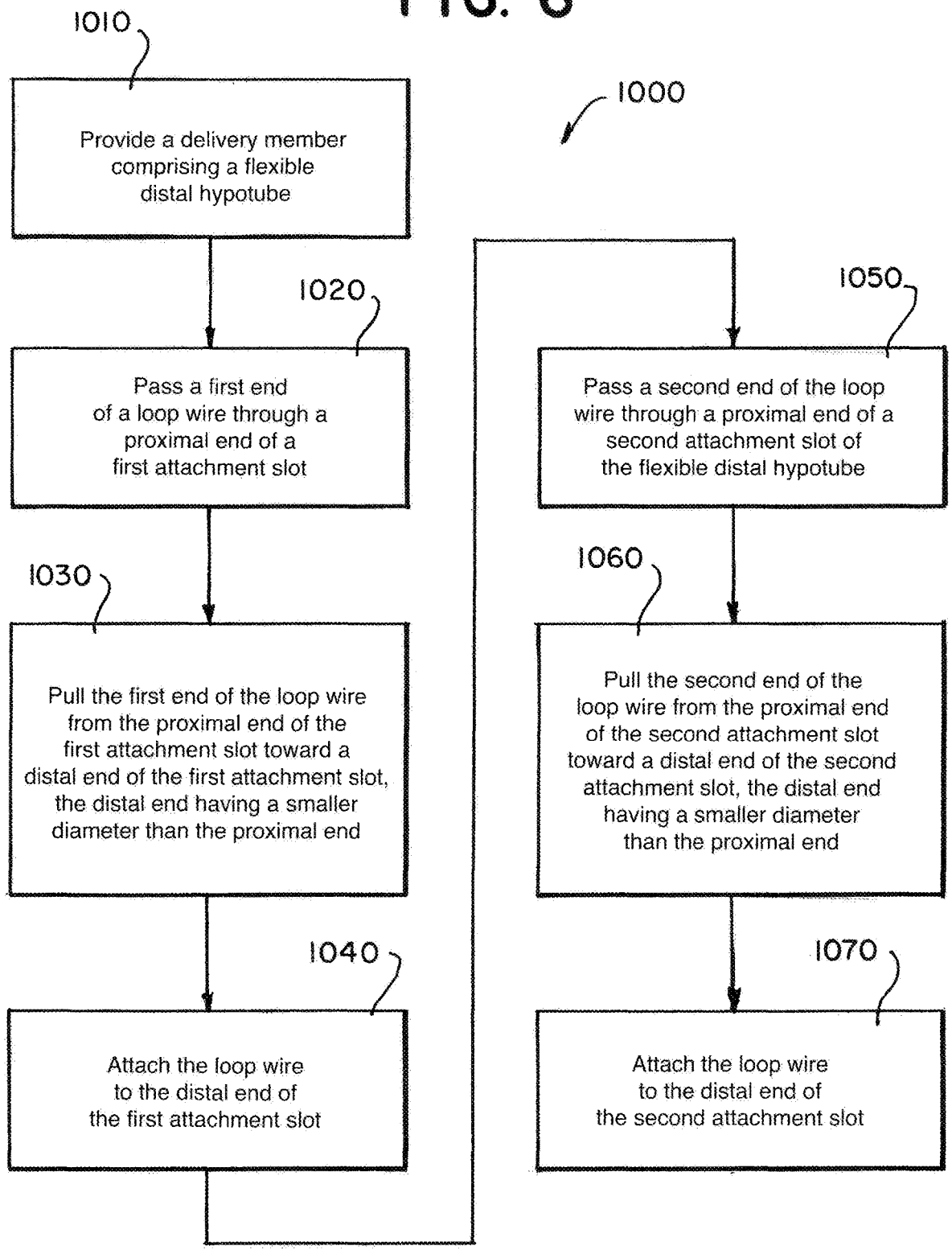

MEDICAL DEVICE DELIVERY MEMBER WITH FLEXIBLE STRETCH RESISTANT DISTAL PORTION

FIELD OF INVENTION

This invention generally relates to intravascular medical device systems that navigable through body vessels of a human subject. More particularly, this invention relates to delivery systems and delivery members for delivering and deploying an implantable medical device to a target location of a body vessel and methods of using the same.

BACKGROUND

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, e.g. brain tissue, it can be difficult and often risky to perform surgical procedures to treat defects of the cranial blood vessels. Advancements in catheter-based implant delivery systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting a delivery catheter into the vasculature of a patient and guiding it through the vasculature to a predetermined delivery site. A vascular occlusion device, such as an embolic coil, can be attached to an implant engagement/deployment system (referred to herein equivalently as an "engagement system" or "deployment system") at a distal end of a delivery member (e.g. micro-catheter) which pushes the coil through the delivery catheter and out of the distal end of the delivery catheter into the delivery site. Example delivery members and engagement/deployment systems are described in U.S. patent application Ser. Nos. 15/850,993, 15/964,857, and 16/502,767, each of which are incorporated herein by reference.

Some of the challenges that have been associated with properly executing such treatment procedures include ensuring the delivery member and engagement system remain in a stable position throughout a treatment. For example, in some aneurysm treatment applications, as the aneurysm becomes increasingly packed with embolic material, the delivery member can tend to shift due to increasing pushback from the embolic material being implanted. If the delivery member shifts during treatment, a physician may not be able to accurately control placement of embolic material and may choose to cease packing the aneurysm. In such an example, the aneurysm may not be sufficiently packed, which can lead to recanalization. Further, excessive movement or stretching of the delivery member and/or engagement system thereon can result in premature detachment of the embolic coil.

There is therefore a need for improved methods, devices, and systems to provide an implant delivery member and implant engagement system with increased stability.

SUMMARY

It is an object of the present invention to provide systems, devices, and methods to meet the above-stated needs. Generally, it is an object of the present invention to provide a delivery member for delivering and deploying an implantable medical device having a flexible distal portion.

Stiffness of the distal portion of the delivery member can cause the microcatheter used for delivery of the embolic material to pull back out of the aneurysm as the distal end of the delivery member is advanced through the tortuous distal anatomy. If the microcatheter pulls back while advancing the embolic material, the microcatheter may come out of the aneurysm and the physician may lose control of the embolic coil and not be able to accurately control placement of embolic material and may not be able to complete treatment.

Flexibility can be provided by incorporating a length of wound coil along the distal portion of the delivery member. The wound coil can be protected by a flexible polymer sleeve positioned around the outside of the coil. The wound coil can be inhibited from elongating by a stretch resistant tube affixed to hypotubes on either end of the wound coil.

An example delivery member for delivering an implantable medical device to a target location of a body vessel can include a proximal hypotube, a support coil section, a distal hypotube, and an engagement system. The support coil section can be affixed to a distal end of the proximal hypotube. The distal hypotube, support coil section, and proximal hypotube can form a contiguous tubular structure having a lumen therethrough. The distal hypotube can include a distal end shaped to receive the implantable medical device. The distal hypotube can include a first attachment slot that extends from the lumen to an outer surface of the distal hypotube. The distal hypotube can include a second attachment slot that extends from the lumen to an outer surface of the distal hypotube. The engagement system can move to engage and deploy the implantable medical device. The engagement system can include a loop wire and a pull wire. The loop wire can extend through an opening in the implantable medical device thereby engaging the engagement system to the implantable medical device. The loop wire can have a first end and a second end. The first end can extend at least partially through the first attachment slot; the second end can extend at least partially through the second attachment slot. The pull wire can extend through the lumen and engage the loop wire, thereby engaging the engagement system to the implantable medical device. The pull wire can be moveable to retract proximally to disengage the loop wire to deploy the implantable medical device.

The first attachment slot can have a distal end and a proximal end. The proximal end can have a first diameter and the distal end can have a second diameter. The first diameter of the first attachment slot can be larger than the second diameter of the first attachment slot. Similarly, the second attachment slot can have a distal end and a proximal end. The proximal end can have a first diameter and the distal end can have a second diameter. The first diameter of the second attachment slot can be larger than the second diameter of the second attachment slot.

The delivery member can include a first attachment connecting the first end of the loop wire to the first attachment slot and a second attachment connecting the second end of the loop wire to the second attachment slot.

The loop wire can be a metallic material, and the first attachment and/or the second attachment can be a weld.

The first attachment and/or the second attachment can include an epoxy.

The first attachment can be a first knot in the loop wire having a knot diameter approximately equal to the first diameter of the first attachment slot. The second attachment can be a second knot in the loop wire having a diameter approximately equal to the first diameter of the second attachment slot.

The loop wire can be a polymer material.

The distal hypotube can include a spiral cut along a longitudinal axis passing through the lumen.

The first attachment slot can be at a position on the distal hypotube opposite the second attachment slot along a diameter line passing through the longitudinal axis. The first attachment slot can be positioned proximal to the second attachment slot at a distance equal to one-half of a pitch of the spiral cut.

The first attachment slot can be at a first position equidistant from two adjacent cuts of the spiral cut. The second attachment slot can be at a second position equidistant from two adjacent cuts of the spiral cut.

The first attachment slot and the second attachment slot can be perpendicular to the longitudinal axis.

An example distal hypotube for a delivery member can have a distal end shaped to receive an implantable medical device. The distal hypotube can have a lumen extending through the distal hypotube. The distal hypotube can include a first attachment slot extending from the lumen to an outer surface of the distal hypotube. The distal hypotube can include a second attachment slot extending from the lumen to the outer surface. The distal hypotube can have a loop wire. The loop wire can be attached at a first end to the first attachment slot and attached at a second end to the second attachment slot. The distal hypotube can have a spiral cut in the outer surface. The spiral cut can be cut along a longitudinal axis passing through the lumen.

The first attachment slot can have a distal end and a proximal end. The proximal end of the first attachment slot can have a larger diameter than the distal end of the first attachment slot. The second attachment slot can have a distal end and a proximal end. The proximal end of the second attachment slot can have a larger diameter than the distal end of the second attachment slot. The loop wire can be attached to the first attachment slot via a first attachment. The loop wire can be attached to the second attachment slot via a second attachment.

The loop wire can be a metallic material, and the first attachment and/or the second attachment can be a weld.

The first attachment and/or the second attachment can include an epoxy.

The first attachment can be a first knot in the loop wire having a knot diameter approximately equal to the first diameter of the first attachment slot. The second attachment can be a second knot in the loop wire having a diameter approximately equal to the first diameter of the second attachment slot.

The first attachment slot can be at a position on the distal hypotube opposite the second attachment slot along a diameter line passing through the longitudinal axis. The first attachment slot can be positioned proximal to the second attachment slot at a distance equal to one-half of a pitch of the spiral cut.

An example method for attaching an implantable medical device on a delivery member includes providing the delivery member. The delivery member can include a flexible distal hypotube. The method can include passing a first end of a loop wire through a proximal end of a first attachment slot of the flexible distal hypotube. The method can include pulling the first end of the loop wire from the proximal end of the first attachment slot toward a distal end of the first attachment slot, the distal end having a smaller diameter than the proximal end. The method can include attaching the loop wire to the first attachment slot. The method can include passing a second end of the loop wire through a proximal end of a second attachment slot of the flexible distal hypotube. The method can include pulling the second end of the loop wire from the proximal end of the second attachment slot toward a distal end of the second attachment slot, the distal end having a smaller diameter than the proximal end. The method can include attaching the loop wire to the second attachment slot.

Attaching the loop wire to the first attachment slot can include welding the loop wire within the first attachment slot.

The method can include tying a first knot in the first end of the loop wire prior to pulling the first end of the loop wire from the proximal end of the first attachment slot toward the distal end of the first attachment slot. The method can include tying a second knot in the second end of the loop wire prior to pulling the second end of the loop wire from the proximal end of the second attachment slot toward the distal end of the second attachment slot.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of a cross section of a delivery member according to aspects of the present invention;

FIG. 2A is an illustration of a cross section of a flexible sleeve according to aspects of the present invention;

FIG. 2B is an illustration of a cross section of a stretch resistant tube according to aspects of the present invention;

FIG. 2C is an illustration of a cross section of a wire coil affixed to a distal hypotube and a proximal hypotube according to aspects of the present invention;

FIGS. 2D through 2H are illustrations of a distal hypotube with a first and second attachments slot according to aspects of the present invention;

FIGS. 3A through 3D are illustrations of an engagement system illustrating a sequence for deploying an implant according to aspects of the present invention;

FIG. 4 is a flow diagram illustrating a method for designing or constructing a delivery member according to aspects of the present invention;

FIG. 5 is a flow diagram illustrating a method for using a delivery system including an example delivery member according to aspects of the present invention; and FIG. 6 is a flow diagram illustrating a method for attaching an implantable medical device to a delivery member.

DETAILED DESCRIPTION

During an intravascular treatment, for instance, an aneurysm occlusion treatment, lack of flexibility of a distal portion of a treatment device delivery member can cause the delivery member to pull back from the treatment site or otherwise move out of position while an implant or other medical treatment device is being placed in an aneurysm or other treatment site. A delivery member and engagement system having a more flexible distal portion can therefore provide a stable system for delivering medical devices in neurovascular anatomy in addition to other applications facing a similar challenge. Flexible structures, however can tend deform, extend, or expand when navigating tortuous anatomy. Deformation of the delivery member can inhibit the delivery member's ability to navigate to a treatment site and/or effectively deploy the medical device. Elongation of the delivery member can result in premature deployment of the medical device.

An object of the present invention is to provide a delivery member having a highly flexible distal portion that is stretch resistant and structurally stable throughout delivery and deployment of a medical treatment device. For ease of discussion, medical treatment devices are generally referred to herein as an "implant" although, as will be appreciated and understood by a person of ordinary skill in the art, aspects of the present invention can be applied to deliver and deploy medical treatment devices that are not left implanted.

According to the present invention, in some examples, the highly flexible distal portion of the delivery member can include a coiled wire, an outer sleeve, and an inner stretch resistant member. The coiled wire can be formed of a substantially linear wire that is wound in a coil shape and/or a hypotube that is laser cut in a spiral pattern. If the coiled wire is formed from a laser cut hypotube, the spiral can be absent interference cuts connecting windings in the coil so as to provide a more flexible coil. The outer sleeve can inhibit the coiled wire from deforming radially and/or provide a smooth surface against which vascular walls can slide during delivery of an implant. The stretch resistant member can inhibit elongation of the coiled wire during delivery of the implant. The combination of the coiled wire, outer sleeve, and stretch resistant member can therefore provide a distal portion of a delivery member having greater flexibility and greater stability than at least some known delivery members.

Turning to the figures, as illustrated in FIG. 1, an example delivery member 10 can include a proximal tube 100, a coiled section 200, a distal tube 300, a sleeve 500 surrounding the coiled section, and a stretch resistant member 600 within the lumen of the coiled section 200. In this disclosure, the terms proximal tube and proximal hypotube can be used interchangeably; similarly, the terms distal tube and distal hypotube can be used interchangeably. The proximal tube 100 can extend a majority of the length of the delivery member 10 with the coiled section 200 and distal tube 300 forming a length sufficient to absorb a majority of push-back that can occur during placement of an implant at a treatment site. In some examples, the length can measure between about 30 cm and about 50 cm, or more specifically, about 40 cm. The proximal tube 100 can have a distal end 104 that is connected to a proximal end 202 of the coiled section 200, and the coiled section 200 can have a distal end 204 that is connected to a proximal end 302 of the distal tube 300. As will be described in greater detail herein, the distal tube 300 can include a compressible portion 306. The compressible portion 306 can be formed from a spiral cut 307 in the distal tube 300, a wound wire, spiral ribbon, or other arrangement allowing axial adjustment according to the present invention. A loop wire 400, which can secure an implant or other medical treatment device to the delivery member 10, can be placed within the lumen 308 of the distal tube 300. The compressible portion 306 of the distal tube 300 can include attachment slots (e.g., a first attachment slot 310 and a second attachment slot 316) enabling the loop wire 400 to pass through the distal tube 300 from the lumen 308 to an outer surface 309 of the distal hypotube.

FIG. 2A is a cross sectional view of the sleeve 500. FIG. 2B is a cross sectional view of the stretch resistant member 600. FIG. 2C is a cross sectional view of the assembled proximal tube 100, coiled section 200, and distal tube 300.

The coiled section 200 can be formed separately from the proximal hypotube 100 and/or the distal hypotube 300. The separately formed coiled section 200 can be affixed with welds 712, 714 or other appropriate attachment to the proximal tube 100 and/or the distal tube 300. Alternatively, or additionally, at least a portion of the coiled section can be formed from a spiral laser cut portion of a hypotube. A separately formed coiled section 200 can be made more flexible compared to a spiral cut tube by selecting a wire with a particular cross section (e.g. circular) with a particular diameter D, or by selecting a wire with material properties to increase flexibility. Conversely, a laser cut portion can be more easily fabricated by cutting a single hypotube to form the proximal tube 100, coiled section 200, and distal hypotube 300, reducing or eliminating welds 712, 714 or other attachments. In either case, the wire of the coil 200 can have a diameter D measuring within a range including about 0.8 mils and 5 mils (about 20 nm to about 130 nm).

The coiled section can be formed primarily of a non-radiopaque material such as steel and can include a radiopaque section 216 made of a radiopaque material such as platinum and/or tungsten. The radiopaque section 216 can be positioned between a proximal, non-radiopaque section of the coil 212 and a distal, non-radiopaque section of the coil 214. The radiopaque section 216 can be positioned a predetermined distance from a distal end 304 of the delivery member 10 so that a physician can readily visualize the placement of the distal portion of the delivery member during a treatment procedure. The proximal section 212, radiopaque section 216, and distal section 214 can be concentrically welded.

The coiled section 200 can be surrounded by a flexible sleeve or fused jacket 500, referred generically herein as a "sleeve." The sleeve 500 can inhibit the coil 200 from expanding radially and/or from engaging vascular walls during navigation. The sleeve 500 can include a polymer. The polymer can include additives to increase the lubricity of the sleeve 500 so that the sleeve can easily slide through a body vessel. As illustrated in FIG. 2A, the sleeve 500 can have a wall thickness T measuring within a range including about 0.5 mils and about 2 mils (about 0.01 mm to about 0.05 mm). The sleeve 500 can further be coated with a hydrophilic coating to further minimize friction during intravascular navigation. The sleeve 500 can be fused or glued to the coil 200, the proximal hypotube 100, and/or the distal hypotube 300.

The stretch resistant member 600 can be positioned to inhibit elongation of the coil 200 during intravascular navigation. The stretch resistant member 600 can include a tube sized to fit within the lumen 208 of the coil 200. The stretch resistant tube 600 can also be sized to extend through the entirety of the length of the coil 200, extend with a lumen 108 of the proximal tube 100 and within the lumen 308 of the distal tube 300. The stretch resistant member 600 can be attached to the proximal tube 100 and the distal tube 300 at adhesive joints 702, 704 or other appropriate attachment. The stretch resistant member 600 can remain unattached to the coiled section 200 such that the stretch resistant member 600 and coiled section 200 are able to move independently from each other to some extent.

The delivery member 10 can include a mechanical engagement system for engaging a medical device 12 during delivery to a treatment site, and the delivery member 10 can be actuated mechanically to deploy the medical device 12. Mechanically actuated engagement systems can include one or more inner elongated members or pull wires extending through the delivery member that can be manipulated at the proximal end by a physician to deploy a medical treatment device. Such a wire or inner elongated member is referred to herein generically as a "pull wire." When reference is made herein to an engagement system, the engagement system can include the combination of a loop wire 400 and a pull wire 140.

FIGS. 2D through 2H illustrate an example distal hypotube 300 that can be used to secure a loop wire 400. The loop wire 400 can be positioned to secure an implant or other medical treatment device to the delivery member 10 and can be moved to release the medical device 12 from the implant or other medical treatment device. This convention will be described in greater detail below in reference to FIGS. 3A-3D. To summarize, the loop wire 400 can extend over a locking portion 18 of a medical device 12. A pull wire 140 can then be slid through an opening 405 at the distal end 404 of the loop wire 400. This can hold the medical device 12 in place until the pull wire 140 is retracted to release the medical device 12.

FIG. 2D is a side view of a distal hypotube 300 with a first attachment slot 310 and a second attachment slot 316 (the second attachment slot 316 is in the background of the figure). The attachment slots 310, 316 can be openings in the outer surface 309 of the distal hypotube 300 that extend from the lumen 308 to the outer surface 309. The attachment slots 310, 316 can facilitate attaching the loop wire 400 to the distal hypotube 300. The attachment slots 310, 316 can be laser cut, for example, into the outer surface 309 of the distal hypotube 300.

The first attachment slot 310 can have a distal end 312 and a proximal end 314. As can be seen, a diameter 313 of the distal end 312 can be smaller than a diameter 315 of the proximal end 314 of the first attachment slot 310. This tapered design can facilitate the attachment of the loop wire 400 to the distal hypotube 300. For example, if the proximal end 314 is larger in diameter, the loop wire 400 can be fed through more easily. Once through the larger proximal diameter 315, the loop wire 400 can be pulled toward the distal end (312) of the first attachment slot (310). In some examples, the transition between the proximal end 314 and the distal end 312 can be slightly tapered such that, as the loop wire 400 is pulled toward the distal end 312, the loop wire 400 can be wedged within the first attachment slot. The second attachment slot 316 can be similar in all regards to the first attachment slot 310. For example, the second attachment slot 316 can have a distal end 322 and a proximal end 324, and a diameter 323 of the distal end 322 can be smaller than a diameter 325 of the proximal end 324 of the second attachment slot 316.

When the loop wire 400 is fed through the attachment slot 310, 316, and pulled toward the distal end 312, 322, the loop wire 400 can be attached to the distal hypotube 300 via an attachment 409, 409. FIG. 2E depicts an example first attachment 408 (the second attachment 409 is in the background of this figure). Using the first attachment slot 310 as an example (the second attachment slot 316 can be similar), the loop wire 400 can be pulled toward the distal end 312 and positioned within the first attachment slot 310 at a desired location within the length of the first attachment slot 310. The loop wire 400 can then be attached to the first attachment slot 310 at a first attachment 408. The first attachment 408 and/or the second attachment 409 can be disposed at the distal end of their respective attachment slot 310, 316. It is not necessary, however, that the first attachment 408 and/or the second attachment 409 be disposed at the most distal end of the slots; the first attachment 408 and/or the second attachment 409 can be placed at a middle section of the slot (i.e., more proximal), as shown in FIG. 2E.

The first attachment 408 can be a weld that holds the loop wire 400 to the first attachment slot 310. In some examples, the loop wire 400 can comprise metallic materials, such as stainless steel, cobalt-chrome alloy, titanium, nickel-titanium alloy (nitinol), and the like. Similarly, the distal hypotube can comprise metallic materials, such as stainless steel, cobalt-chrome alloy, titanium, nitinol, and the like. This can enable the first attachment 408 to be a metallic weld attaching the loop wire 400 to the first attachment slot 310. In some examples, the loop wire 400 can comprise a polymer material, such as nylon, polypropylene, silk, polyester, and the like. The loop wire can include braided or monofilament wires. The first attachment 408 can be a thermoplastic weld at the first attachment slot 310.

Additionally, or alternatively, the first attachment 408 can be an epoxy holding the end of the loop wire 400 to the first attachment slot 408. As stated above, the second attachment slot 316 can include a second attachment 409 to attach the loop wire 400 to the second attachment slot 316. The second attachment 409 can be similar to the first attachment 408.

In some examples, the first attachment 408 can be a knot in the loop wire 400. As described above, the first attachment slot 310 can have a proximal end 314 that is larger in diameter than the distal end 312. The loop wire 400 can be pulled through the first attachment slot 310, tied into a knot, and then pulled toward the distal end 312. The knot can be larger than the distal diameter 313 so that the loop wire 400 cannot be pulled back through the first attachment slot 310 once a knot is tied in the loop wire 400. In other examples, the loop wire 400 can be tied into a knot first, then the knot can be fed through the proximal end of 314 of the first attachment slot 310, and then the loop wire 400 can be pulled toward the distal end 312. In these examples, a knot diameter can be approximately equal to the first diameter 315 of the first attachment slot 310. This would enable the loop wire 400 to be fed through the proximal end 314 but prohibit the loop wire 400 from being pulled through the distal end 312 of the first attachment slot 310. The second attachment 409 can similarly be a knot in the opposite end of the loop wire 400.

FIG. 2F is a side view of an example distal hypotube 300. The first attachment slot 310 is in the foreground of this figure; the second attachment slot 316 is in the background. As described above, a distal hypotube 300 can have a flexible and/or compressible portion 306. The compressible portion 306 can be formed from a spiral cut 307 in the distal hypotube 300, a wound wire, spiral ribbon, or other arrangement allowing axial adjustment according to the present invention. In some examples, the placement of the first attachment slot 310 and/or the second attachment slot 316 can be selected based on a pitch of the spiral cut 307. To improve the flexibility of the distal hypotube 300, for example, the first attachment slot 310 can be offset from the second attachment slot 316 by a ratio of the pitch of the spiral cut 307, as shown by slot offset 320. As shown in the figure, an example of this slot offset 320 is that the first attachment slot 310 can be positioned opposite the second attachment slot 316, and the first attachment slot 310 can be offset proximal to the second attachment slot 316 at a distance approximately equal to half of the pitch 318 of the spiral cut 307. It is not necessary, however, that the first attachment slot 310 be positioned opposite the second attachment slot 316. The first attachment slot 310 can be disposed at a first position equidistant from two adjacent cuts of the spiral cut 307, and the second attachment slot 316 can disposed at a second position equidistant from two adjacent cuts of the spiral cut 307. This can be true for any position on the distal hypotube 300, whether or not the attachment slots 310, 316 are opposite from each other on the other surface 309.

FIG. 2G is a perspective view of a distal hypotube 300 showing the example offsetting of the first attachment slot 310 and second attachment slot 316. Offsetting the first attachment slot 310 and the second attachment slot 316 with respect to the pitch of the spiral cut 307 can increase the flexibility of the distal hypotube 300 by not impeding its flexing about the spiral cut 307.

FIG. 2H is a side cross-sectional view of an example distal hypotube 300. In some examples, the first attachment slot 310 and the second attachment slot 316 can be formed (for example laser cut, drilled, etc.) into the distal hypotube 300 perpendicular to a longitudinal plane 326*b* passing through the lumen 308 of the distal hypotube 300. The longitudinal plane 326*b* is the three-dimensional view of the longitudinal axis 326*b* passing through the lumen 308. Perpendicular cuts can help facilitate the attachment of the loop wire 400 to the first attachment slot 310 and the second attachment slot 316. For example, once the loop wire 400 is fed through the first attachment slot 310 and the second attachment slot 316, perpendicular cuts can help ensure uniform surface contact between the loop wire 400 and the outer walls of the attachment slots 310, 316.

FIG. 2H also provides a good view of an example slot offset 320 between the first attachment slot 310 and the second attachment slot 316. As described above, a first attachment slot 310 can be disposed at a position on the distal hypotube 300 opposite the second attachment slot 316 along a diameter line passing through the longitudinal axis 326*a*. The first attachment slot 310 and the second attachment slot 316 can be offset based on the pitch of the spiral cut 307.

FIGS. 3A through 3D illustrate the delivery member 10 including a mechanical engagement system including a pull wire 140 and a loop wire 400 that can be positioned to secure an implant or other medical treatment device to the delivery member 10 and can be moved to release the medical treatment device from the delivery member 10. The loop wire 400 can be affixed to the distal tube 300 with first attachment 408 and a second attachment 409. The stretch resistant member 600 can be sized to allow a pull wire 140 to pass through the lumens 108, 208, 308 of the proximal tube 100, coiled section 200, and distal tube 300. For instance, the stretch resistant member 600 can be tubular, having a lumen therethrough, and the pull wire 140 can extend through the lumen of the tubular stretch resistant member 600. During manufacture of the stretch resistant member 600, the stretch resistant member 600 can be extruded over the pull wire 140.

The combination of the coil 200, sleeve 500, and stretch resistant member 600 can provide a highly flexible distal portion of a delivery member 10 suitable for navigating tortuous anatomy, including neurovascular blood vessels.

The stretch resistant member 600 can support the coil 200 to prevent the coil 200 from significantly extending during navigation of a blood vessel, thereby reducing tension on a pull wire 140 extending therethrough and reducing the likelihood of premature deployment of an attached medical treatment device.

The proximal tube 100 can include a flexible section 106 having material removed to increase flexibility of the flexible section 106. The flexible section 106 can be cut in a spiral pattern. The spiral pattern of the flexible section 106 can lack interference cuts connecting windings within the spiral. The stretch resistant member 600 can extend through the flexible section 106 and be attached to the proximal tube 100 in the proximal direction from the flexible section 106. The stretch resistant member 600 can thereby inhibit elongation of the flexible section 106 of the proximal tube 100 and coiled section 200. The sleeve 500 can cover at least a portion of the flexible section 106 to inhibit deformation of the flexible section and/or reduce friction with vasculature and the flexible section 106 during intravascular navigation. In some examples, the sleeve 500 can cover about 10 cm of the proximal tube 100 approximate and/or including the distal end 104 of the proximal tube 100.

The distal hypotube 300 can include a compressible portion 306. The compressible portion 306 can be axially adjustable between an elongated condition and a compressed condition. The distal hypotube 300 can also be flexible such that the distal hypotube 300 can provide a stable system for delivering medical devices in neurovascular anatomy. The distal hypotube 300 can include a spiral cut 307, formed by a laser cutting operation for example, to create the compressible and/or flexible construct. Additionally, or alternatively, the compressible portion 306 can be formed of a wound wire, spiral ribbon, or other arrangement allowing axial adjustment according to the present invention. Preferably, the compressible portion 306 is in the elongated condition at rest and automatically or resiliently returns to the elongated condition from a compressed condition, unless otherwise constrained.

FIGS. 3A-3D, illustrate the detachment of the medical device 12 using a mechanical engagement/deployment system. FIG. 3A illustrates the engagement system 140, 400 locked into the locking portion 18 of the medical device 12. The compressible portion 306 of the distal tube 300 can be compressed and the loop wire 400 opening 405 at a distal end 404 of the loop wire 400 can be placed through the locking portion 18. When the pull wire 140 is put through the opening 405 the medical device 12 is now secure. FIG. 3B illustrates the pull wire 140 being drawn proximally to begin the release sequence for the medical device 12. FIG. 3C illustrates the instant the pull wire 140 exits the opening 405 and is pulled free of the loop wire 400. The distal end 404 of the loop wire 400 falls away and exits the locking portion 18. As can be seen, there is now nothing holding the medical device 12 to the delivery member 10 (e.g., the distal hypotube 300). FIG. 3D illustrates the end of the release sequence. Here, the compressible portion 306 has extended/returned to its original shape and "sprung" forward. An elastic force E is imparted by the distal end 304 of the distal tube 300 to the medical device 12 to "push" it away to ensure a clean separation and delivery of the medical device 12.

Illustrations in the above-described figures depict generally hollow or tubular structures 100, 200, 300, 500, 600 according to the present invention. When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

FIG. 4 is a flow diagram including method steps for constructing or designing a delivery member such as the example delivery members described herein. Referring to the method 800 outlined in FIG. 4, in step 810, a first hypotube, a second hypotube, a flexible sleeve, a wire coil, and a stretch resistant member can be selected. The first hypotube can be a proximal hypotube 100 as described herein or as would otherwise be known to a person of ordinary skill in the art. The second hypotube can be a distal hypotube 300 as described herein or as would otherwise be known to a person of ordinary skill in the art. The flexible sleeve can be a sleeve or fused jacket 500 as described herein or as otherwise known to a person of ordinary skill in the art. The wire coil can include the support coil, coiled section 200 as described herein or as otherwise known to a person of ordinary skill in the art. The stretch resistant member can be a stretch resistant member 600 as described herein or as otherwise known to a person of ordinary skill in the art.

In step 820, the stretch resistant member can be positioned in the lumen of the wire coil. In step 820, the stretch resistant member that is positioned can be substantially tubular. In step 830, the first hypotube, wire coil, and second hypotube can be attached to each other. In step 840, the stretch resistant member is attached to the first hypotube and the second hypotube. The first hypotube, wire coil, and second hypotube can be attached as illustrated and described herein or by other means as would be understood by a person of ordinary skill in the art. Steps 820, 830, and 840 need not be performed in that order and can be performed simultaneously. For instance, the stretch resistant member can be attached to one of the first and second hypotubes as indicated in step 840, then the hypotube to which the stretch resistant member is attached can be attached to the wire coil as indicated in step 830, then the stretch resistant member can be positioned through the wire coil as indicated in step 820, then the other of the hypotubes can be attached to the wire coil as indicated in step 830, then the stretch resistant member can be attached to that other hypotube as indicated in step 840.

In step 850, the wire coil can be covered with the flexible sleeve. The flexible sleeve can cover some or all of the outer surface of the wire coil. Step 850 can also include the step of fusing the flexible sleeve to the wire coil and/or otherwise affixing the flexible sleeve to the delivery member. If the second hypotube has a flexible section, in step 850, the flexible sleeve can also be positioned to cover at least a portion of the flexible section.

In step 860, an implant can be detachably attached to the distal end of the first hypotube. In step 860, the implant can be attached by positioning a loop wire within the first hypotube, positioning a pull wire to extend through the first hypotube, coiled wire, and second hypotube, and securing the implant with the loop wire and the pull wire. The pull wire can be extended from the proximal end of the second hypotube. If the first hypotube has a compressible portion, in step 860, the compressible portion can be compressed, and the implant can be attached to delivery member while the compressible portion is compressed.

FIG. 5 is a flow diagram including method steps for administering an intravascular treatment using a system including a delivery member such as the example delivery members described herein. Referring to the method 900 outlined in FIG. 5, in step 910 a system having a distal hypotube, proximal hypotube, coiled section co-axially positioned in between the hypotubes, a flexible sleeve covering the coiled section, a stretch resistant member positioned within the coiled section, and a medical treatment device attached to or near the distal hypotube can be selected. The system can be suitable for intravascular treatments such as described and illustrated herein or as otherwise known to a person of ordinary skill in the art.

In step 920, the system can be moved through a catheter to a treatment site such as the site of an aneurysm or other abnormality in a blood vessel. In step 930, the system can be flexed as it is moved through the catheter. In step 940, the coiled section of the system can be prevented from deforming by the flexible sleeve and the stretch resistant member; the flexible sleeve can inhibit the coiled section from deforming radially while the stretch resistant member can inhibit the coil from extending longitudinally.

In step 950, the medical treatment device can be deployed. In the case that the medical treatment device is an implant, in step 950 the implant can be detached. In step 960, the distal tube can extend to push the medical treatment device away from the distal tube. In the case that the medical treatment device is an implant detached in step 950, in step 960, the detached implant can be ejected away from the distal tube in response to the expansion of the distal tube.

FIG. 6 is a flow diagram including method steps for attaching an implantable medical device to a delivery member. Referring to method 1000 outlined in FIG. 6, in step 1010, the delivery member can be provided. The delivery member can include a flexible distal hypotube, as described herein. In step 1020, a first end of a loop wire can be passed through a proximal end of a first attachment slot of the distal hypotube. In step 1030, the first end of the loop wire can be pulled from the proximal end toward a distal end of the first attachment slot. As stated above, the distal end of the first attachment slot can have a smaller diameter than the proximal end.

In step 1040, the loop wire can be attached to the first attachment slot. This attachment can be made in a number of ways, as described herein. The loop wire can be welded to the first attachment slot. In other examples, the loop wire can be affixed to the first attachment slot via an epoxy. In other examples, the loop wire can include a knot tied into the first end of the loop wire. The knot can be tied prior to pulling the first end of the loop wire through the proximal end of the first attachment slot. In this case, the knot can be approximately the same size as the diameter of the proximal end of the first attachment slot. This can enable the knot to be fed through the proximal end but prohibit the knot from being pulled back through the distal end. The knot can be tied after pulling the first end of the loop wire through the proximal end of the first attachment slot. The knot can be larger than one or both of the proximal and the distal end of the first attachment slot so that the loop wire cannot be pulled back through the first attachment slot. The first end of the loop wire can be attached at the distal end of first attachment slot, or the first end of the loop wire can be attached at any other location in the first attachment slot that is narrower than the proximal end (see, for example, FIG. 2E). In step 1050 through step 1070, the method steps outlined above for steps 1020 through 1040 can be repeated for a second attachment slot. For example, a second end of the loop wire can be positioned in a second attachment slot similar to the process described above for the first end of the loop wire and the first attachment slot.

The descriptions contained herein are examples of embodiments of the invention and are not intended in any way to limit the scope of the invention. As described herein, the invention contemplates many variations and modifications of the delivery system, delivery member, and engagement system, including alternative configurations of components, alternative materials, alternative medical treatment devices, alternative means for deploying the medical treatment device, alternative geometries of individual components, alternative means for attaching component parts, etc. These modifications would be apparent to those having ordinary skill in the art to which this invention relates and are intended to be within the scope of the claims which follow.

What is claimed is:

1. A delivery member for delivering an implantable medical device to a target location of a body vessel, the delivery member comprising:
    a proximal hypotube;
    a support coil section affixed to a distal end of the proximal hypotube;
    a distal hypotube comprising:
        a distal end shaped to receive the implantable medical device;
        a first attachment slot extending from a lumen of the distal hypotube to an outer surface of the distal hypotube; and
        a second attachment slot extending from the lumen to the outer surface of the distal hypotube; and
    an engagement system movable to engage and deploy the implantable medical device engaged at the distal end of the distal hypotube, the engagement system comprising:
        a loop wire extended through an opening in the implantable medical device thereby engaging the engagement system to the implantable medical device, a first end of the loop wire extending at least partially through and attached to the first attachment slot via a first weld or a first epoxy, and a second end of the loop wire extending at least partially through and attached to the second attachment slot via a second weld or a second epoxy; and
        a pull wire extended through the lumen, engaged to the loop wire thereby engaging the engagement system to the implantable medical device, and movable to retract proximally to disengage the loop wire to deploy the implantable medical device.

2. The delivery member of claim 1, wherein the first attachment slot comprises a distal end and a proximal end, the proximal end of the first attachment slot having a first diameter and the distal end of the first attachment slot having a second diameter, the first diameter of the first attachment slot being larger than the second diameter of the first attachment slot, and wherein the second attachment slot comprises a distal end and a proximal end, the proximal end of the second attachment slot having a first diameter and the distal end of the second attachment slot having a second diameter, the first diameter of the second attachment slot being larger than the second diameter of the second attachment slot.

3. The delivery member of claim 1, wherein the loop wire comprises a metallic material.

4. The delivery member of claim 1, wherein the loop wire comprises a polymer material.

5. The delivery member of claim 1, wherein the distal hypotube further comprises a spiral cut along a longitudinal axis passing through the lumen.

6. The delivery member of claim 5,
    wherein the first attachment slot is disposed at a position on the distal hypotube opposite the second attachment slot along a diameter line passing through the longitudinal axis, and
    wherein the first attachment slot is positioned proximal to the second attachment slot at a distance equal to one-half of a pitch of the spiral cut.

7. The delivery member of claim 5,
    wherein the first attachment slot is disposed at a first position equidistant from two adjacent cuts of the spiral cut, and
    wherein the second attachment slot is disposed at a second position equidistant from two adjacent cuts of the spiral cut.

8. The delivery member of claim 7, wherein the first attachment slot and the second attachment slot are disposed perpendicular to the longitudinal axis.

9. A distal hypotube for a delivery member, the distal hypotube comprising:
    a distal end shaped to receive an implantable medical device;
    a lumen extending through the distal hypotube;
    a first attachment slot extending from the lumen to an outer surface of the distal hypotube;
    a second attachment slot extending from the lumen to the outer surface of the distal hypotube;
    a loop wire attached at a first end to the first attachment slot via a first weld or a first epoxy and attached at a second end to the second attachment slot via a second weld or a second epoxy; and
    a spiral cut in the outer surface of the distal hypotube cut along a longitudinal axis passing through the lumen.

10. The distal hypotube of claim 9, wherein the first attachment slot comprises a distal end and a proximal end, the proximal end of the first attachment slot having a first diameter and the distal end of the first attachment slot having a second diameter, the first diameter of the first attachment slot being larger than the second diameter of the first attachment slot, and wherein the second attachment slot comprises a distal end and a proximal end, the proximal end of the second attachment slot having a first diameter and the distal end of the second attachment slot having a second diameter, the first diameter of the second attachment slot being larger than the second diameter of the second attachment slot.

11. The distal hypotube of claim 9, wherein the loop wire comprises a metallic material.

12. The distal hypotube of claim 9,
    wherein the first attachment slot is disposed at a position on the distal hypotube opposite the second attachment slot along a diameter line passing through the longitudinal axis, and
    wherein the first attachment slot is positioned proximal to the second attachment slot at a distance equal to one-half of a pitch of the spiral cut.

* * * * *